United States Patent
Chen et al.

(10) Patent No.: US 8,896,836 B1
(45) Date of Patent: Nov. 25, 2014

(54) FLUID PROPERTIES MEASUREMENTS USING WAVELENGTH MODULATION SPECTROSCOPY WITH FIRST HARMONIC DETECTION

(71) Applicant: Southwest Sciences Incorporated, Santa Fe, NM (US)

(72) Inventors: Shin-Juh Chen, Santa Fe, NM (US); Joel A. Silver, Santa Fe, NM (US)

(73) Assignee: Southwest Sciences Incorporated, Santa Fe, NM (US)

( * ) Notice: Subject to any disclaimer, the term of this patent is extended or adjusted under 35 U.S.C. 154(b) by 0 days.

(21) Appl. No.: 13/868,326

(22) Filed: Apr. 23, 2013

Related U.S. Application Data

(60) Provisional application No. 61/636,937, filed on Apr. 23, 2012.

(51) Int. Cl.
  *G01N 21/61* (2006.01)
  *G01N 21/35* (2014.01)

(52) U.S. Cl.
  CPC ............ *G01N 21/61* (2013.01); *G01N 21/3504* (2013.01)
  USPC ....................................................... 356/437

(58) Field of Classification Search
  CPC ........................... G01N 21/61; G01N 21/3504
  USPC .................................................. 356/432–444
  See application file for complete search history.

(56) References Cited

U.S. PATENT DOCUMENTS

| | | | |
|---|---|---|---|
| 5,178,002 A * | 1/1993 | Hanson | 73/112.04 |
| 5,708,495 A | 1/1998 | Pitz et al. | |
| 6,356,350 B1 * | 3/2002 | Silver et al. | 356/437 |
| 7,012,696 B2 | 3/2006 | Orr et al. | |
| 7,230,712 B2 * | 6/2007 | Cannon | 356/437 |
| 7,251,034 B2 * | 7/2007 | Kluczynski et al. | 356/437 |
| 7,508,521 B2 * | 3/2009 | Liu et al. | 356/437 |
| 7,560,869 B2 | 7/2009 | Miles et al. | |
| 7,616,316 B1 * | 11/2009 | Silver et al. | 356/437 |
| 8,265,851 B2 * | 9/2012 | Girouard et al. | 701/99 |

OTHER PUBLICATIONS

Barhorst, et al., "Development of an In Flight Non-instrusive Mass Capture System", 45th AIAA/ASME.SAE/ASEE Joint Propulsion Conference & Exhibit, Aug. 2009.

Bomse, et al., "Frequency modulation and wavelength modulation spectroscopies: comparison of experimental methods using a lead-salt diode laser", Applied Optics, Feb. 20, 1992, 718-731.

Chen, et al., "Laser-Based Mass Flow Rate Sensor Onboard HIFiRE Flight 1", 45th AIAA/ASME/SAE/ASEE Joint Propulstion Conference & Exhibit, Aug. 2, 2009.

Drummond, et al., "Hypersonic Airbreathing Propulsion—An Aerodynamics, Aerothermodynamics, and Acoustics Competency White Paper", NASA/TM-2002-211951, Nov. 2002.

(Continued)

*Primary Examiner* — Sang Nguyen
(74) *Attorney, Agent, or Firm* — Jeffrey D. Myers; Peacock Myers, P.C.

(57) ABSTRACT

An apparatus and method for monitoring gas velocity, temperature, and pressure in combustion systems and flow devices, in particular at inlets and isolators of scramjet engines. The invention employs wavelength modulation spectroscopy with first harmonic detection and without the need to scan the full absorption spectra.

20 Claims, 5 Drawing Sheets

(56) References Cited

OTHER PUBLICATIONS

Grisch, "Molecular Diagnostics for the Study of Hypersonic Flows", Paper presented at the RTO AVT Course on "Measurement Techniques for High Enthalpy and Plasma Flows", Oct. 25, 1999, 5-1=5-19.

Hanson, "Applications of quantitative laser sensors to kinetics, propulsion and practical energy systems", Proceedings of the Combustion Institute, 2011, 1-40.

Hanson, et al., "Hypersonic Mass-Flux Sensing with Fiber-Coupled Tunable Diode Lasers for Ground Test Applications and Flight Evaluation", NASA Fundamental Aeronautics 2007 Annual Meeting, 2007.

Jacquinet-Husson, et al., "The 2009 edition of the GEISA spectroscopic database", Journal of Quantitative Spectroscopy & Radiative Transfer, 2011, 2395-2445.

Kloesel, et al., "A Technology Pathway for Airbreathing, Combined-Cycle, Horizontal Space Launch Through SR-71 Based Trajectory Modeling", AIAA 2011-2229, 17th AIAA International Space Planes and Hypersonic Systems and Technologies Conference, 2011.

Li, et al., "Uncertainty in velocity measurement based on diode-laser absorption in nonuniform flows", Applied Optics, Jul. 10, 2012, 4788-4797.

Lindstrom, et al., "Diode Laser Absorption Tomography of 2D Supersonic Flow", 43rd AIAA/ASME/SAE/ASEE Joint Propulsion Conference & Exhibit, Jul. 2007.

Mohamed, et al., "Laser Absorption Spectroscopy to Probe Chemically Reacting Flows", Journal Aerospace Lab, Dec. 2009, 1-12.

Rothman, et al., "The HITRAN 2008 molecular spectroscopic database", Journal of Quantitative Spectroscopy & Radiative Transfer, 2009, 533-572.

Silver, "Frequency-modulation spectroscopy for trace species detection: theory and comparison among experimental methods", Applied Optics, Feb. 20, 1992, 707-717.

Sippel, et al., "Preliminary Definition of a TBCC Propulsion System for a Mach 4.5 Supersonic Cruise Airliner", ISABE 2007-1204, International Society for Air Breathing Engines, 2007.

Wheatley, "Tunable Diode Laser Absorption Spectroscopy of Hypersonic Flows", 28th International Congress of the Aeronautical Sciences, 2012.

Williams, et al., "Diode Laser Diagnostics of High Speed Flows", Proceedings of the 14th AIAA/AHI Internaitonal Space Planes and Hypersonic Systems and Technologies Conference, Oct. 2006.

* cited by examiner

FLUID PROPERTIES MEASUREMENTS USING WAVELENGTH MODULATION SPECTROSCOPY WITH FIRST HARMONIC DETECTION

CROSS-REFERENCE TO RELATED APPLICATIONS

This application claims priority to and the benefit of the filing of U.S. Provisional Patent Application Ser. No. 61/636,937, entitled "Fluid Properties Measurements Using Wavelength Modulation Spectroscopy with First Harmonic Detection", filed on Apr. 23, 2012, and the specification and claims thereof are incorporated herein by reference.

STATEMENT REGARDING FEDERALLY SPONSORED RESEARCH OR DEVELOPMENT

This invention was made with government support under Contract No. FA8650-11-M-2146 awarded by the U.S. Air Force and No. NNX13CS03P awarded by the National Aeronautics and Space Administration (NASA). The government has certain rights in the invention.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

1. Field of the Invention (Technical Field)

The present invention relates to methods and apparatuses for determining the velocity, temperature and pressure of gases in supersonic inlets of scramjet engines, and any other gas flows requiring the knowledge of pressure, velocity and temperature.

2. Description of Related Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Turbine-based combine cycle (TBCC) and rocket-based combined cycle (RBCC) are airbreathing propulsion technologies for two-stage-to-orbit vehicles that operate at costs lower than conventional methods based solely on rockets and scramjets. TBCC is applicable in the flow regime from subsonic to supersonic and not suitable for orbital insertion, but is the choice for a high speed passenger transport (Sippel, M. and Okai, K., "Preliminary Definition of a TBCC Propulsion System for a Mach 4.5 Supersonic Cruise Airliner," ISABE 2007-1204, International Society for Air Breathing Engines). RBCC is suitable for hypersonic to rarefied flow regimes. RBCC based vehicles are capable of reaching high altitudes and space with pure rocket operation (Kloesel, K. J., Ratnayake, N. A., and Clark, C. M., "A Technology Pathway for Airbreathing, Combined-Cycle, Horizontal Space Launch Through SR-71 Based Trajectory Modeling," AIAA 2011-2229, 17th AIAA International Space Planes and Hypersonic Systems and Technologies Conference, San Francisco, Calif.). The need for the non-intrusive measurement of velocity, pressure and temperature profiles at the inlet and exhaust flows is obvious when supersonic flow speeds are present. Traditional probes used for temperature, pressure and velocity disturb the flow sufficiently that corrections, based on a priori measurements and models, are needed to ascertain the local flow properties. Moreover, wall-based measurements of pressure do not provide information on local nonuniformities. Even in uniform flows, pressure in the core flow is determined via corrections using models with the knowledge of the adjacent wall pressure. Temperature and velocity measurements based on optical methods such as particle imaging velocimetry (PIV) and planar laser-induced fluorescence (PLIF) are excellent for a small region of interest but not easily amenable to a full profile of the inlet and exhaust flows. Accurate information of inlet flow properties is important for gauging the mass capture and properly tuning the fuel flow for efficient combustion. Flow properties of exhaust flows are important for assessing the thrust generated by the combustion system (Drummond, J. P., Cockrell, C. E., Jr., Pellett, G. L., et al., "Hypersonic Airbreathing Propulsion—An Aerodynamics, Aerothermodynamics, and Acoustics Competency White Paper," NASA/TM-2002-211951).

Velocity and temperature measurements via tunable diode laser absorption spectroscopy (TDLAS) are well established for measuring gas temperatures and velocities in combustor flows. Both direct absorption and wavelength modulation spectroscopy (WMS) methods exist to make these measurements (Hanson, R. K., "Applications of quantitative laser sensors to kinetics, propulsion and practical energy systems," Proc. Combust. Inst. 33, 1-40 (2011); Li, F., et al., "Uncertainty in velocity measurement based on diode-laser absorption in nonuniform flows," Appl. Opt. 51, 4788-4797 (2012); Barhorst, T., Williams, S., Chen, S.-J., Paige, M. E., and Silver, J. A., "Development of an In Flight Non-Intrusive Mass Capture System," AIAA Paper No. 2009-5067, 45th AIAA/ASME/SAE/ASEE Joint Propulsion Conference & Exhibit (2009); Silver, J. A., "Frequency Modulation Spectroscopy for Trace Species Detection Theory and Comparison Among Experimental Methods," Appl. Opt. 31, 707-717 (1992); Bomse, D. S., Stanton, A. C., and Silver, J. A., "Frequency Modulation and Wavelength Modulation Spectroscopies: Comparison of Experimental Methods Using a Lead-Salt Diode Laser," Appl. Opt. 31, 718 (1992)). These studies always require the recording of the full absorption spectrum, and for temperature measurements often require two lasers. For high speed (>1 kHz) transient measurements, the electronic requirements for high precision and sensitivity become cumbersome at best, where data acquisition rates and demodulation electronics push beyond MHz frequencies. The analyses of these measurements can be quite complex, requiring measurement of a host of spectroscopic parameters and their dependence on temperature and pressure in order to retrieve the local gas temperature. This makes the sensor systems inflexible and suitable for only one gas, whereas multiple gases may be of interest. All of the aforementioned measurements apply to velocity or temperature. There have been no reported methods to optically measure local pressure.

Hanson (U.S. Pat. No. 5,178,002) discussed a system and method for determining the value of thrust non-intrusively from products of combustion of a jet engine. Both line-of-sight absorption spectroscopy and laser-induced fluorescence methods are discussed for measuring pressure, velocity, and temperature of a gas. Full absorption spectra are used in the measurements.

Williams, S., et al., "Diode Laser Diagnostics of High Speed Flows," AFRL-PR-WP-TP-2007-204, Air Force Research Laboratory, Propulsion Directorate, October 2006, discussed the use of direct absorption spectroscopy with full line shapes and multiplexing of multiple lasers for the measurement of mass capture in hypersonic inlets and isolators.

Lindstrom, C., et al., "Diode Laser Absorption Tomography of 2D Supersonic, Flow," 43$^{rd}$ AIAA/ASME/SAE/ASEE Joint Propulsion Conference & Exhibit, 8-11 Jul. 2007, Cincinnati, Ohio, examined the combined use of tomography reconstruction techniques and direct absorption spectroscopy with full line shape to probe supersonic flows for determining flow properties and species concentrations.

Chen, S.-J., et al., "Laser-Based Mass Flow Rate Sensor Onboard HIFiRE Flight 1," 45$^{th}$ AIAA/ASME/SAE/ASEE Joint Propulsion Conference & Exhibit, 2-5 Aug. 2009, Denver, Colo., used wavelength modulation spectroscopy with second harmonic detection and full line shape to measure gas velocity in high speed flows. The measurements were carried onboard a sounding rocket reaching a speed of Mach 8.

Wheatley, B., "Tunable Diode Laser Absorption Spectroscopy of Hypersonic Flows," 28$^{th}$ International Congress of the Aeronautical Sciences," ICAS, 2012, reviewed the method of tunable diode laser absorption spectroscopy for the measurement of flow properties and species concentrations in hypersonic and scramjet flows. Direct absorption spectroscopy and wavelength modulation spectroscopy using first and second harmonic detection, using full line shape, were compared.

Girouard, R., et al. (U.S. Pat. No. 8,265,851) disclosed a method for controlling the performance of engines via the measurement of a wavelength-dependent parameter. Based on the measured parameter, a needed adjustment to the combustion event is determined and physically applied to the engine to enhance engine performance. Direct absorption spectroscopy and wavelength modulation spectroscopy were identified as some of the measurement methods to obtain velocity, temperature, and species concentrations, all using full line shapes.

The present invention improves on the art by, e.g., using an optical velocity measuring system that comprises a light source from a diode laser and two detectors to monitor two crossed-beams paths. Alternatively, pressure can be measured using a single path across the flow. The present invention provides the following advantages over the state-of-the-art sensors: (1) not requiring the need to scan the full absorption line shape; (2) no need to fit the data to obtain peak positions of measured absorption line; (3) no modeling of line shapes to account for residual amplitude modulation; (4) capable of achieving high-bandwidth measurements of 10 kHz or higher; (5) measuring only two point values per probed path; (6) inherently self-calibrating; (7) no contributions from interference fringes (etalons) which show up only as dc offset; and (8) high-sensitivity using wavelength modulation spectroscopy with 1f detection.

BRIEF SUMMARY OF THE INVENTION

The present invention is of a method (and concomitant apparatus) for non-intrusively obtaining the local velocity, pressure, and temperature of a gas, comprising: emitting two beams of laser light directed at two different angles across a flow of the gas; separately detecting the two beams; determining first harmonic line shapes from the detected beams using wavelength modulation spectroscopy and a pair of single point measurements; calculating gas velocity and pressure from Doppler shifts of the line shapes; and calculating gas temperature from slopes of the line shapes; wherein wavelength of the two beams is alternated between two fixed wavelengths; and using a reference cell to provide zero-velocity reference and pressure reference. In the preferred embodiment, a square wave is employed, most preferably wherein frequency of the square wave is at or greater than desired detection bandwidth. Scanning full absorption line shapes is not required. Gas velocity is determined independent of gas density changes. Calculating gas temperature comprises employing a mole fraction of the gas and/or measuring second harmonic peak signals. The invention preferably operates at a bandwidth of up to about 40 kHz, obtains velocity at a resolution of about 10 m/s fluctuation or better, and obtains pressure at about plus or minus 12 torr at 2 atmospheres.

Further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

The present invention is of a method of and apparatus for monitoring non-intrusively gas velocity, pressure and temperature in combustion systems and flow devices. It is capable of measuring these parameters (velocity, pressure, and temperature) without the need to record the full absorption spectra of the probed chemical species. It is capable of monitoring these parameters at faster speeds compared to traditional methods which record the full absorption spectra. It is capable of measuring these parameters simultaneously using the same optical paths and setups. It is capable of providing a means to communicate with the systems or devices for the purpose of active-control to enhance efficiencies. It is capable of interrogating multiple locations simultaneously within the combustion systems and flow devices.

Figure 1:
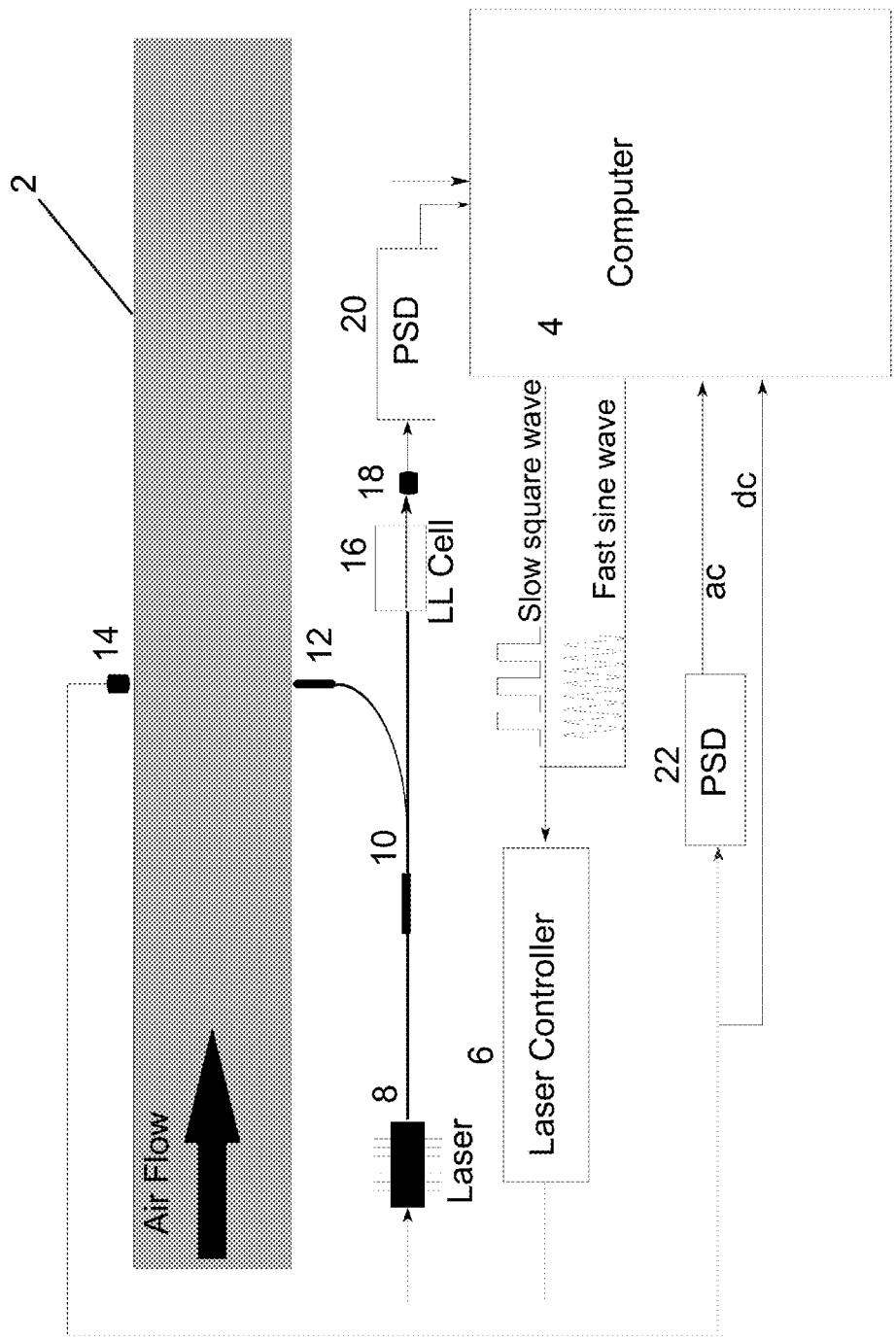
FIG. 1 is a schematic diagram illustrating the apparatus for measuring pressure and/or temperature using a single optical path that is perpendicular to the flow path.

In the preferred apparatus for pressure and temperature measurements, as illustrated in FIG. 1, a computer 4 (or other waveform generating source) generates a slow square wave (i.e., low frequency) and fast sine wave (i.e., high frequency). A laser controller 6 uses the slow square wave and fast sine wave to control a laser source 8. A beam splitter 10 directs the laser beam into two paths. One path sends the light into a line-locking cell 16 and another portion of the light into a light collimator 12 for focusing. Light exits the beam collimator 12 and traverses the probed region 2 and is collected by a detector 14. Light traversing the line-locking cell is collected by another detector 18. The AC-component of signal from the detector 18 is processed by a phase-sensitive detector 20 and sent to the computer 4 for additional processing. The AC-component of light collected by detector 14 is also processed by a phase-sensitive detector 22. The DC-component of the signal from detector 14 is processed directly by the computer 4.

Figure 2:
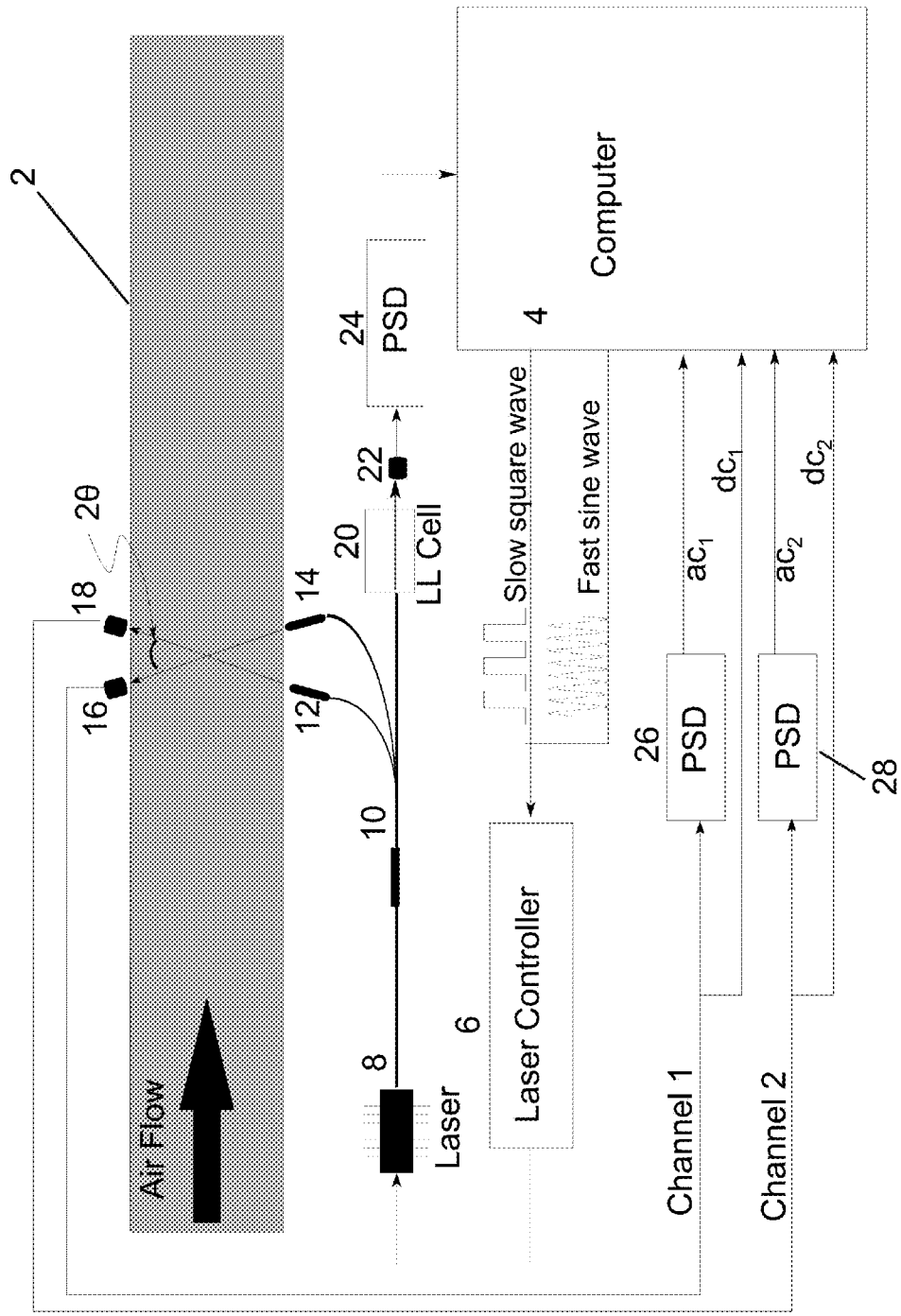
FIG. 2 is a schematic diagram illustrating the apparatus for measuring velocity, pressure, and temperature using two optical paths angled in opposite direction to the flow path.

In the preferred apparatus for velocity measurements, as illustrated in FIG. 2, a computer 4 (or other waveform generating source) generates a slow square wave (i.e., low frequency) and fast sine wave (i.e., high frequency). A laser controller 6 uses the slow square wave and fast sine wave to control a laser source 8. A beam splitter 10 directs the laser beam into three separate paths. Two light collimators 12 and 14 are used to direct the laser beam into two measurement paths that are crossed by an angle 2θ to probe air flow 2. Two detectors 16 and 18 are used to collect signals from these two measurement paths. Phase-sensitive electronics 26 and 28 are used to collect the measurement AC-signals. The DC-signals are processed directly by a computer 4. A third beam is directed through a line-locking cell 20 and onto detector 22. The AC-signal from detector 22 originating from line-locking cell 20 is collected by phase-sensitive detection electronics 24 and processed by computer 4.

In the preferred embodiment the beam injection system comprises a focusing lens for collimating the laser output beam from preferably a fiber optic cable, preferably matched for the operating wavelength. The detection system comprises a photodetector, preferably matched for the operating wavelength. For pressure measurements, the coupler 10 in FIG. 1 comprises a fiber splitter having 90 percent and 10 percent output legs. For velocity measurements (FIG. 3), the first coupler comprises a fiberized splitter having 45, 45, and 10 percent output legs. Alternatively, this 3-way splitter could be replaced with two splitters, the first having 90 percent and 10 percent output legs. The 90 percent leg is subsequently split by a second 50-50 splitter to provide intensity to the crossed beams in the flow. Any combination of splitting laser power using 2-way and 3-way splitters can be used.

Advantages of this approach include measurement bandwidth of 10 kHz or faster, high-sensitivity measurements with absorbance of 1 part 1,000 at 10 kHz are possible, inherently self-calibrating step, and insensitivity to optical interferences like etalons. The method uses a single point measurement without the need to scan the full absorption line shape as it is typically done in TDLAS based measurements.

Traditionally, high sensitivity detection using optical absorption uses wavelength modulation spectroscopy. The main features of WMS are that spectral noise is reduced by performing signal detection at frequencies, high enough to avoid laser excess (1/f) noise fluctuations in the laser output power (>10 kHz) and that the measurements are made against a zero-valued baseline. To perform WMS, a small high-frequency sinusoidal modulation is superimposed on the diode laser injection current. This current modulation produces a modulation of the laser wavelength at the same frequency since the laser wavelength is tuned by changing the current. Absorption by the target gas converts the wavelength modulation to an amplitude modulation of the laser intensity incident on the detector, adding AC components to the detector photocurrent. Phase-sensitive detection of the detector photocurrent at a multiple n of the modulation frequency selectively amplifies the AC components and shifts the measurement from near DC to higher frequencies where laser noise is reduced.

One can also detect at the primary modulation frequency, 1f. In this case the WMS line shape looks like the first derivative of the direct absorption line shape, where the signal crosses the baseline at the absorption peak wavelength. Here the slope efficiency of the laser appears as a dc offset. This offset can also be used as a monitor of $I_0$. Since the 1f-WMS signal crosses its baseline when the laser wavelength is at line center, this signal is often used in a line-locking feedback loop to keep the laser scan centered on the peak. A key feature of the 1f line shape is that the line shape near the zero crossing is a linear function (i.e., essentially a straight line with no curvature).

Typically, one scans the laser wavelength (laser injection current) across the spectral line of interest and records the absorption spectrum. For very high bandwidth measurements, this approach is problematic. A typical spectrum requires 100-1000 points. To acquire a full spectrum for a desired 10 kHz bandwidth, one must scan at a minimum rate of 10 kHz, with each data point acquired at 1-10 MHz. To avoid data aliasing, the modulation frequency must be at least three times higher than this rate. A full spectral scan thus requires high speed electronics, and scanning the laser this fast reduces its tunability and introduces noise. Data processing requirements are also more complex and expensive. A feature of this invention is that there occurs no scanning across the line shape, but the laser wavelength is simply alternated between two very closely-spaced wavelengths on either side of line center. This feature minimizes the effect of etalons, no line shape fitting is required, and high bandwidths are readily achieved.

Figure 3:
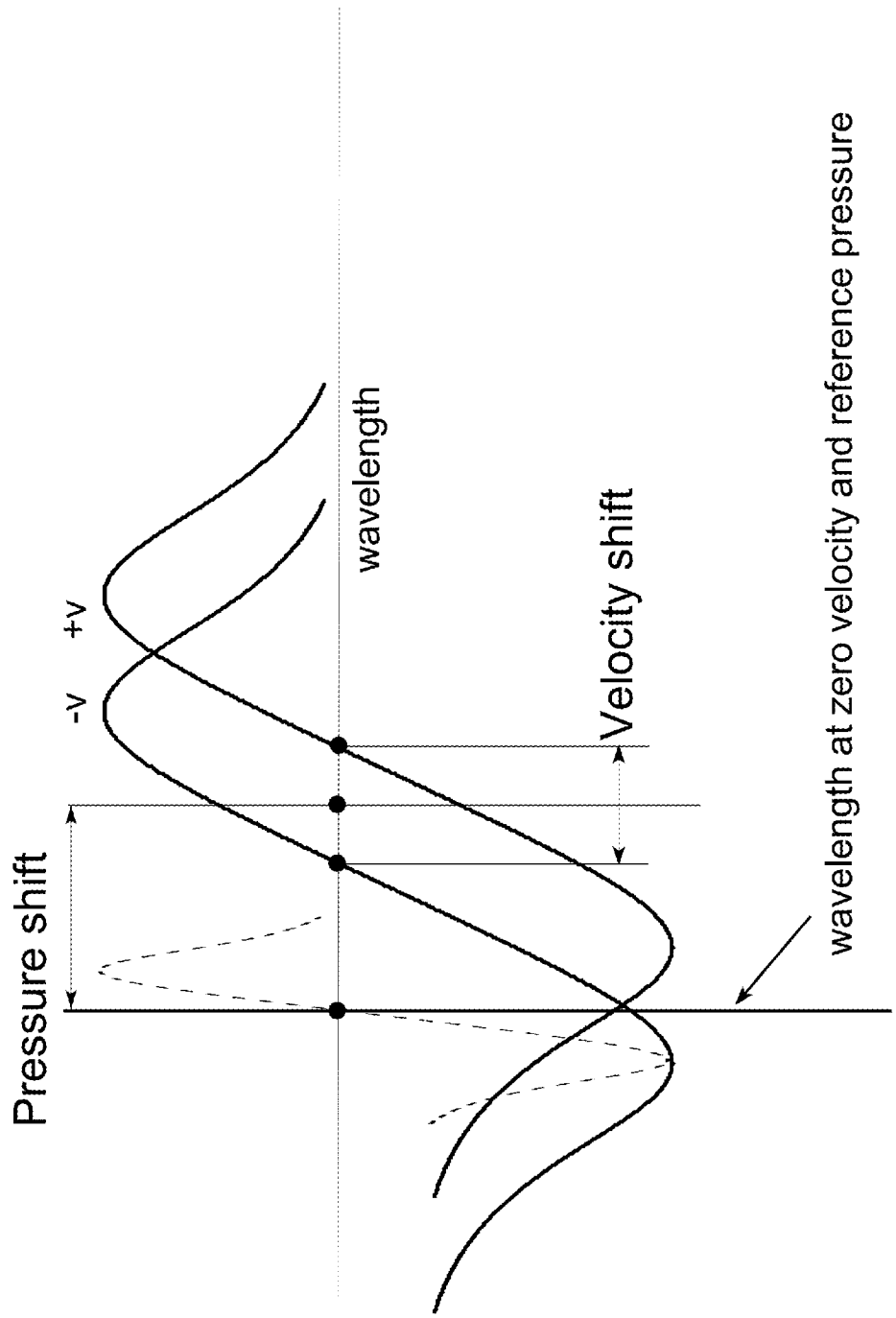
FIG. 3 is a schematic diagram illustrating the velocity-induced and pressure-induced shift of wavelength with respect to wavelength at zero velocity and at reference pressure using wavelength modulation spectroscopy with 1f detection.

Gas velocity measurements using absorption employ the Doppler effect to relate the frequency shift in the line center absorption wavelength to the speed of the gas, as illustrated in FIG. 3. A laser beam traverses the gas flow at an angle other than 0 degrees, and the observed shift in measured line center frequency in wavenumbers $v_0$ is determined by the component of the velocity vector along the flow direction. The shifted line frequency $\Delta v_D$ is proportional to the incidence angle θ by, $$\Delta v_D = v_0(1+\overline{V}\sin\theta/c)(1+b_S(P/P_0)), \quad (1)$$

where $\overline{V}$ is the mean gas velocity, $b_S$ is the shift coefficient defined for pressure $P_0$, P is the local pressure, c the speed of light, and $v_0$ the peak absorption frequency in wavenumbers. This equation accounts for the Doppler shift in a gas flow as well as for the effect of pressure-shifting, where the absolute line center wavenumber of an absorption peak varies linearly with local pressure. Pressure shift coefficients (in units of $cm^{-1}/atm$) are tabulated in the HITRAN and GEISA databases for many common gases (Rothman. L. S., et al., "The HITRAN 2008 molecular spectroscopic database," J. Quant. Spectrosc. Radiat. Trans. 110, 533-572 (2009); Jacquinet- Husson, N., et al., "The 2009 edition of the GEISA spectroscopic database," J. Quant. Specrosc. Radiat. Trans. 112, 2395-2445 (2009)).

Using a pair of beams crossed at angle 2θ, as illustrated in FIG. 2, both beams shift in the same direction for changes in pressure, but the Doppler shifts of the crossed beams in a moving gas are in opposite directions. For two beams crossed at 60 degrees (θ=±30°), the relative separation in line centers due to velocity only is $$\Delta v_{D,pair} = v_0 * \overline{V}/c \quad (2)$$

FIG. 3 shows 1f-WMS line shapes for such a system of crossed beams, referenced to the line shape of a static, fixed-pressure gas. Note the reference line shape (dashed line) can have a different width (slope) than the sample beams (solid lines). This figure illustrates how the crossed beams separate in wavelength due to their relative (+) and (−) velocity shifts in the flow, while both beams move in the same direction if their pressure is different than in the reference leg.

Figure 4:
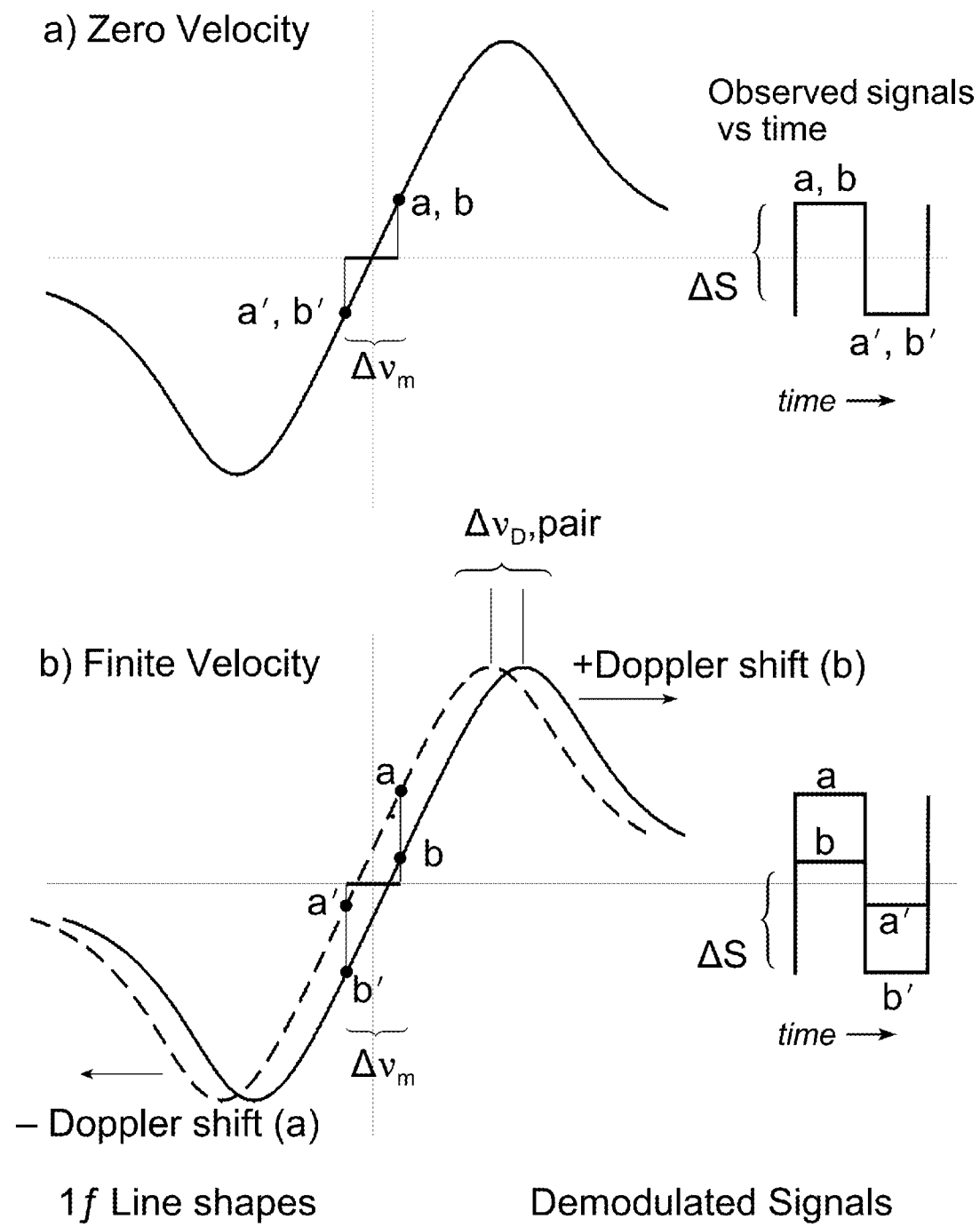
FIG. 4 is a schematic diagram illustrating the method of Doppler shift for measuring velocity using wavelength modulation spectroscopy with 1f detection and two points along the linear portion of the curve.

Measuring gas velocity at high bandwidths via the Doppler shift using a full spectrum is limited by noise, electronics and processing constraints. The present innovation eliminates all of these complications and permits easy and precise high bandwidth measurements. This is illustrated in FIG. 4a where the 1f-WMS signal is shown for a system that uses (for this illustration) a 5 kHz detection bandwidth. The 1f-WMS signal near the center of the line shape varies linearly with wavenumber. This effect is explained by the fact that the peak of a Voigt line shape can be accurately represented by a parabolic function (i.e., $y=mx^2+b$). The first derivative (WMS shape) of this function is a straight line with $y'=2mx$, where x=wavenumber and 2m is the slope. The slope of the 1f shape is related to the gas density.

Rather than scan the laser across the full absorption spectrum, one could fix the laser at a single wavelength on the if line shape. As the velocity changes, the line shape would shift left or right (as in FIG. 4b) and this signal voltage would change in proportion to the velocity shift. As this is now only a one-point measurement, velocity can be rapidly determined. A full spectrum of many points is not required. However, as temperature, pressure, or concentration change, so does the slope.

At zero flow velocity, both crossed laser beams produce identical line shapes; there is no Doppler shift (FIG. 4a). When the gas velocity is non-zero, the two line shapes separate and shift in opposite directions. Rather than scan across these shapes and record full spectra, the approach here simply alternates the laser wavelength between two fixed wavelengths on either side of line center and monitors the 1f signal voltages at these two wavelengths. For both crossed beam channels which are identical here, one measures line shape voltages of a=b for the positive square wave step and a'=b' for the negative step of the square wave. The difference in signal voltage ΔS between these two values (top and bottom of the measured square wave as a function of time) provides the instantaneous slope, since we know the wavenumber difference $\Delta v_m$ between the alternating steps. This slope in terms of voltage a, a', b, and b' is $$\text{Slope}_{1f} = (\Delta S / \Delta v_m) = (a-a')/\Delta v_m = (b-b')/\Delta v_m. \text{ Units of volts*cm-1} \quad (3)$$

Now as the velocity becomes non-zero (FIG. 4b), the observed square wave voltages for the two beams separate vertically, providing a measure of the velocity shift $\Delta v_D$ (FIG. 4b), where $$(a-b) = \text{Slope}_{1f} * v_D. \quad (4)$$

Combining Eqns. (2)-(4) with a previously measured calibration of $\Delta v_m$, one finds the mean gas velocity is $$\overline{V} = \Delta v_m * c * (a-b)/(v_0 * (a-a')) \quad (5)$$

If, for fixed $\overline{V}$, the slope of the line shape were to vary due to a change in pressure, temperature, or concentration of the gas, the individual square wave voltage ranges (a-a' or b-b') would change, but the (+) and (−) velocity beam waveform separations (a-b or a'-b') would also scale accordingly, so that the resultant velocity would be the same. Therefore, the inventive approach simultaneously measures both the slope and signal level to measure velocity independent of density changes.

In practice, this measurement is accomplished by imposing a small square wave step $\Delta v_m$ on the laser current so that the measurement wavelength alternates above and below line center (noted by orange vertical lines). The frequency of this alternation should be at or greater than the desired detection bandwidth, so as to capture all fluctuations in density that might be correlated to velocity shifts. For example, if one desired a detection bandwidth of 5 kHz, the step frequency could be 10 kHz, and the analog-to-digital (ADC) acquisition rate could be 20 kHz or greater. To be sure that the 1f modulation is properly acquired and demodulated, one can set f=100 kHz. A helpful feature of this approach is only low frequency rf electronics are required, helping assure that noise associated with high bandwidth circuits are avoided. In addition to these 1f-WMS AC-signals from each leg, the corresponding DC-signals are also acquired by separate ADCs for laser intensity normalization. A significant advantage of this method is that if the density (P, T or mole fraction) changes the slope of the line shape, this effect is immediately accounted for in the analysis. Detection bandwidths up to 40 kHz should be readily achieved.

The exact location of the absorption peak at zero velocity can be found by locking the laser wavelength to a 1f signal of a gas sample in a fixed pressure, static reference cell, and using the zero crossing as a feedback signal. This provides a reference for zero velocity and for our calibration pressure, $P_0$.

Figure 5:
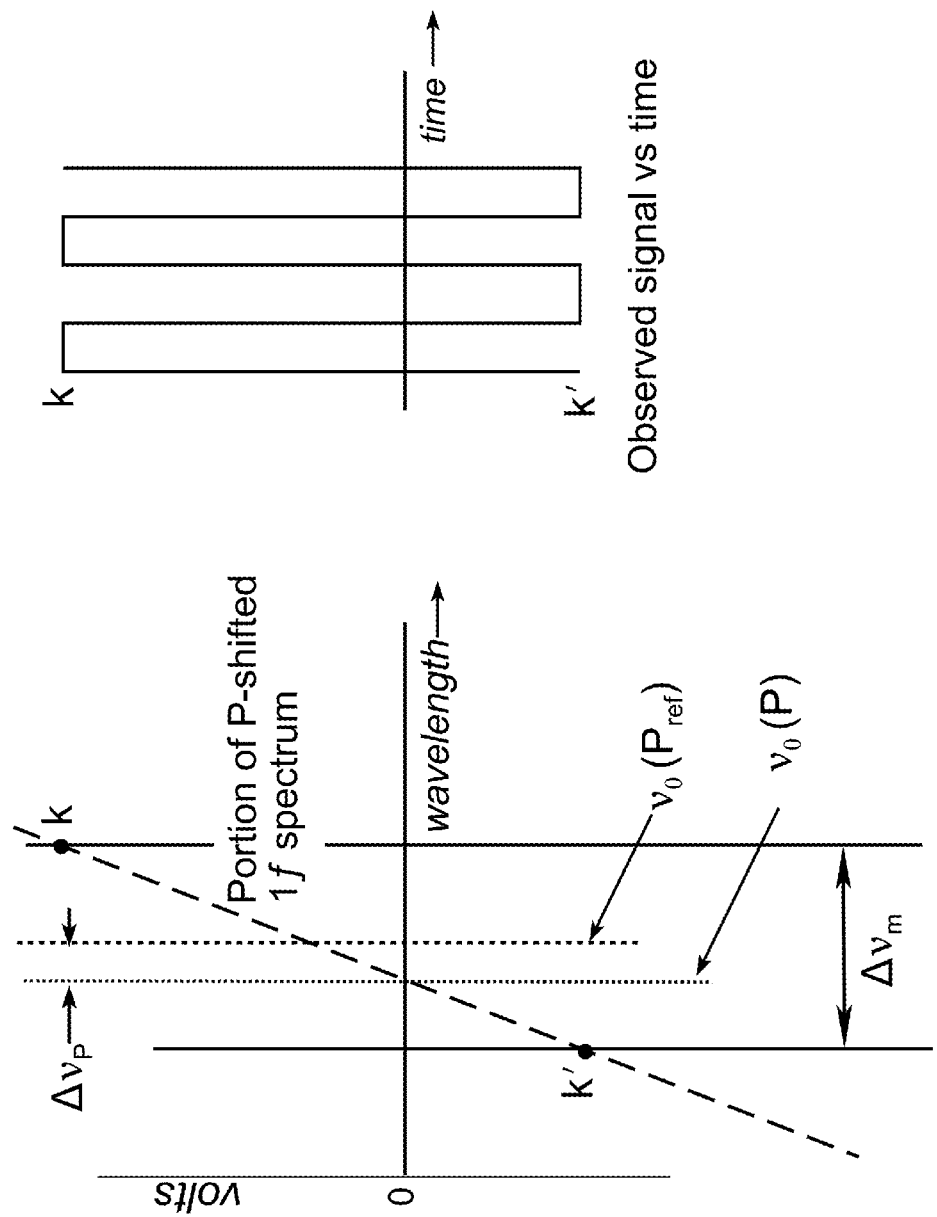
FIG. 5 is a schematic diagram illustrating the method for measuring pressure using wavelength modulation spectroscopy with 1f detection using two points along the linear portion of the curve.

By comparing the square wave signal of one of the velocity measurement lines (after the velocity component is subtracted off) to the reference signal, the pressure shift can be found. Alternatively, one could use a single beam pointed directly across the flow (θ=0, no velocity shift) as shown in FIG. 1. This signal is illustrated in FIG. 5, where just the linear portion of the 1f line shape is shown (dashed line on left side). From this signal and Eqn. (1), the pressure is $$P = P_0 + (\Delta v_P / b_S) \quad (6)$$

where $\Delta v_P$ is the observed wavenumber shift between the reference pressure and flow signal. In a manner similar to that above, the flow pressure in terms of measured voltages k and k' is $$P = P_0 + (\Delta v_m / (2b_s)) * ((k'+k)/(k'-k)) \quad (7)$$

As mentioned above, the mean shift of both crossed beams relative to the zero velocity reference signal could also be used to find the unidirectional pressure shift.

For the purpose of illustrating the method of this invention, the slope of the 1f line shape near line center reflects the number density of the absorbing gas. By selecting an appropriate absorption line tailored to an expected temperature range of interest, one can achieve a situation where the slope of the 1f waveform near line center varies monotonically with density. The difficulty is that this density depends on both temperature and mole fraction of the species being measured.

If one is working with oxygen in the inlet of a hypersonic engine, for example, the mole fraction of oxygen in air is always 0.21, and the slope can be used to determine the local temperature directly. If one is measuring water vapor, there are two unknowns. However, there may be regions where the functional form of the slope versus density curve is such that the variation may be insensitive to either mixing ratio or temperature, so that one may be able to unravel both functions. One can easily make an additional measurement of the 2f peak signals (just some minor additional electronics) that provides the peak absorbance and thus a second observable.

In another example using the 1391.7 nm water vapor absorption line and assuming a pressure of 2 atmospheres and temperature of 1200 K, the fractional absorbance of combustor exhaust water vapor across an 8 cm path is approximately 0.18. The shift in wavenumber with velocity for this line is approximately 0.002 $cm^{-1}$ per 100 m/s. So for a Mach 1 flow, the shift would be about 0.008 $cm^{-1}$. Pressure shifts for water vapor are $-0.017$ $cm^{-1}$/atm, so that a pressure of 2 atmospheres would have a shift (relative to a 0.25 atmosphere reference) of $-0.030$ $cm^{-1}$.

Minimum detectable absorbance for systems using wavelength modulation spectroscopy is typically $10^{-5}$ or better for a 1 Hz bandwidth. Since sensitivity scales as the square root of bandwidth, the expected sensitivity at 5 kHz would be $7 \times 10^{-4}$, equivalent to a SNR (signal to noise ratio) of 250. From these numbers, one predicts a measurement resolution of 0.8%. So for a velocity of 300 m/s, one could ideally resolve at 2.4 m/s. Of course, there is a wide variation in the possible mixing ratios, T, P, paths, and velocities that might exist in the engines being tested, but an expectation of better than 10 m/s fluctuation resolution at high bandwidth appears feasible. This precision should also apply to pressure, which at 2 atmospheres would be ±12 torr.

In the preferred embodiment, and as readily understood by one of ordinary skill in the art, the apparatus according to the invention will include a general or specific purpose computer or distributed system programmed with computer software implementing the steps described above, which computer software may be in any appropriate computer language, including C++, FORTRAN, BASIC, Java, assembly language, microcode, distributed programming languages, etc. The apparatus may also include a plurality of such computers/distributed systems (e.g., connected over the Internet and/or one or more intranets) in a variety of hardware implementations. For example, data processing can be performed by an appropriately programmed microprocessor, computing cloud, Application Specific Integrated Circuit (ASIC), Field Programmable Gate Array (FPGA), or the like, in conjunction with appropriate memory, network, and bus elements.

Note that in the specification and claims, "about" or "approximately" means within twenty percent (20%) of the numerical amount cited. All computer software disclosed herein may be embodied on any non-transitory computer-readable medium (including combinations of mediums), including without limitation CD-ROMs, DVD-ROMs, hard drives (local or network storage device), USB keys, other removable drives, ROM, and firmware.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method for non-intrusively obtaining the local velocity, pressure, and temperature of a gas, the method comprising the steps of:
   emitting two beams of laser light directed at two different angles across a flow of the gas;
   separately detecting the two beams;
   determining first harmonic line shapes from the detected beams using wavelength modulation spectroscopy and a pair of single point measurements by a computer;
   calculating gas velocity and pressure from wavelength shifts of the line shapes by the computer; and
   calculating gas temperature from slopes of the line shapes by the computer;
   wherein wavelength of the two beams is alternated between two fixed wavelengths; and having an additional signal channel to provide reference zero-velocity and reference pressure.

2. The method of claim 1 wherein a square wave is employed.

3. The method of claim 2 wherein frequency of the square wave is at or greater than desired detection bandwidth.

4. The method of claim 1 wherein scanning full absorption line shapes is not required.

5. The method of claim 1 wherein gas velocity is determined independent of gas density changes.

6. The method of claim 1 wherein calculating gas temperature comprises employing a mole fraction of the gas.

7. The method of claim 1 wherein calculating gas temperature comprises measuring second harmonic peak signals.

8. The method of claim 1 wherein the method operates at a bandwidth of up to about 40 kHz.

9. The method of claim 1 wherein velocity is obtained at a resolution of about 10 m/s fluctuation or better.

10. The method of claim 1 wherein pressure is obtained at about plus or minus 12 torr at 2 atmospheres.

11. An apparatus for non-intrusively obtaining the local velocity, pressure, and temperature of a gas, said apparatus comprising:
    two emitters of beams of laser light directed at two different angles across a flow of the gas;
    detectors for the two beams;
    a computer determining first harmonic line shapes from the detected beams using wavelength modulation spectroscopy and a pair of single point measurements, calculating gas velocity and pressure from wavelength shifts of the line shapes, and calculating gas temperature from slopes of the line shapes;
    a laser controller alternating wavelength of the two beams between two fixed wavelengths; and
    a reference cell providing reference zero-velocity and reference pressure.

12. The apparatus of claim 11 wherein a square wave is employed by said laser controller.

13. The apparatus of claim 12 wherein frequency of said square wave is at or greater than desired detection bandwidth.

14. The apparatus of claim 11 wherein scanning full absorption line shapes is not required.

15. The apparatus of claim 11 wherein gas velocity is determined independent of gas density changes.

16. The apparatus of claim 11 wherein calculating gas temperature comprises employing a mole fraction of the gas.

17. The apparatus of claim 11 wherein calculating gas temperature comprises measuring second harmonic peak signals.

18. The apparatus of claim 11 wherein said apparatus operates at a bandwidth of up to about 40 kHz.

19. The apparatus of claim 11 wherein velocity is obtained at a resolution of about 10 m/s fluctuation or better.

20. The apparatus of claim 11 wherein pressure is obtained at about plus or minus 12 torr at 2 atmospheres.

* * * * *